(12) United States Patent
Miersch

(10) Patent No.: US 9,247,987 B2
(45) Date of Patent: Feb. 2, 2016

(54) ELECTROSURGICAL GRIPPING ELEMENT

(75) Inventor: Hannes Miersch, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 64 days.

(21) Appl. No.: 14/111,307

(22) PCT Filed: May 16, 2012

(86) PCT No.: PCT/EP2012/059124
§ 371 (c)(1),
(2), (4) Date: Oct. 11, 2013

(87) PCT Pub. No.: WO2012/156449
PCT Pub. Date: Nov. 22, 2012

(65) Prior Publication Data
US 2014/0031815 A1    Jan. 30, 2014

(30) Foreign Application Priority Data
May 18, 2011 (DE) .......................... 10 2011 076 071

(51) Int. Cl.
*A61B 18/14* (2006.01)
*A61B 18/12* (2006.01)
*A61B 18/00* (2006.01)

(52) U.S. Cl.
CPC ......... *A61B 18/1442* (2013.01); *A61B 18/1206* (2013.01); *A61B 2018/00589* (2013.01); *A61B 2018/00601* (2013.01); *A61B 2018/1467* (2013.01)

(58) Field of Classification Search
CPC ............... A61B 2018/00607; A61B 2018/126; A61B 18/1402; A61B 2018/145; A61B 2018/1445

USPC .............. 606/32, 41, 45, 48, 51–52, 205–208
See application file for complete search history.

(56) References Cited

U.S. PATENT DOCUMENTS 5,700,261 A * 12/1997 Brinkerhoff .................... 606/41
5,766,166 A *  6/1998 Hooven .......................... 606/45
(Continued)

FOREIGN PATENT DOCUMENTS

| CN | 1889893 A | 1/2007 |
| WO | WO 99/23960 A1 | 5/1999 |
| WO | 2005/055846 A1 | 6/2005 |

OTHER PUBLICATIONS

International Search Report issued in International Application No. PCT/EP2012/059124 on Aug. 10, 2012.

(Continued)

*Primary Examiner* — Michael Peffley
(74) *Attorney, Agent, or Firm* — Oliff PLC (57) ABSTRACT

The invention relates to an electrosurgical gripping instrument comprising a handle part as well a lower jaw part and an upper jaw part which can perform a forcipate movement. The gripping instrument has a first pair of coagulation sections with a first lower coagulation section on the lower jaw part and a first upper coagulation section on the upper jaw part and, further, a second pair of coagulation sections with a second lower coagulation section on the lower jaw part and a second upper coagulation section on the upper jaw part. Moreover, the electrosurgical gripping instrument has a bipolar pair of cutting electrodes between the first pair of coagulation sections and the second pair of coagulation sections.

13 Claims, 8 Drawing Sheets

(56) References Cited

U.S. PATENT DOCUMENTS

| | | | |
|---|---|---|---|
| 5,908,420 A * | 6/1999 | Parins et al. | 606/51 |
| 6,152,923 A * | 11/2000 | Ryan | 606/51 |
| 8,192,433 B2 * | 6/2012 | Johnson et al. | 606/51 |
| 2002/0013583 A1 | 1/2002 | Camran et al. | |
| 2004/0049185 A1 | 3/2004 | Latterell et al. | |
| 2007/0156139 A1 | 7/2007 | Schechter et al. | |
| 2008/0195093 A1 * | 8/2008 | Couture et al. | 606/45 |
| 2009/0171352 A1 * | 7/2009 | Sutter | 606/49 |

OTHER PUBLICATIONS

Written Opinion of the International Searching Authority issued in International Application No. PCT/EP2012/059124 on Aug. 10, 2012.

Mar. 26, 2015 Office Action issue in Chinese Patent Application No. 201280023726.6.

\* cited by examiner

ELECTROSURGICAL GRIPPING ELEMENT

The invention relates to an electrochemical gripping instrument comprising a handle part as well as a lower jaw part and an upper jaw part which can perform a forcipate movement. The gripping instrument has a first pair of coagulation sections with a first lower coagulation section on the lower jaw part and a first upper coagulation section on the upper jaw part and, further, a second pair of coagulation sections with a second lower coagulation section on the lower jaw part and a second upper coagulation section on the upper jaw part.

Electrosurgical gripping instruments of the mentioned type usually have a cutting electrode which is arranged between the first pair of coagulation sections and the second pair of coagulation sections. The coagulation sections serve for coagulating tissue, for example a blood-conveying vein, whereas, by means of the cutting electrode, the tissue between the first pair of coagulation sections and the second pair of coagulation sections can be cut. This takes place in that between the cutting electrode and one of the coagulation sections, current is conducted through the tissue. Due to the rapid heating of the cell fluid caused by the current flow and the resulting increasing vapor pressure in the cells, cell walls are ruptured. However, when cutting after coagulation, the current has to overcome tissue regions which are already coagulated. Since the tissue dehydrates during coagulation, coagulated regions have a significantly higher resistance. In the worst case, it can happen that no current flows if the dehydrated tissue represents an insulator.

It is an object of the invention to provide a gripping instrument with improved cutting properties.

According to the invention, this is achieved with an electrosurgical gripping instrument comprising a handle part as well as a lower jaw part and an upper jaw part which can perform a forcipate movement,
  wherein a first pair of coagulation sections with a first lower coagulation section on the lower jaw part and a first upper coagulation section on the upper jaw part is provided,
  wherein further a second pair of coagulation sections with a second lower coagulation section on the lower jaw part and a second upper coagulation section on the upper jaw part is provided,
  and wherein at least one bipolar pair of cutting electrodes is provided between the first pair of coagulation sections and the second pair of coagulation sections.

Such a gripping instrument has the advantage that the current does not have to flow through coagulated tissue during the cutting process.

In the simplest case, the handle part of the electrosurgical instrument has the shape of a shaft. However, alternatively, the handle part can also comprise suitable means that support holding the instrument, for example loops and/or control elements for the electrosurgical gripping instrument or connected power supply units, for example a high-frequency (HF) generator. The lower jaw part and the upper jaw part are typically connected to each other through a joint so that they can perform a forcipate movement. For example, one of the two jaw parts is thereby firmly connected to the handle part, while the respective other jaw part is movable relative thereto around the joint. Alternatively, for example, the lower jaw part can also be rigidly connected to the handle part, while the upper jaw part is rigidly connected to another handle part.

A joint within the context of this application is to be understood as any movable connection of two parts, here at least the lower jaw part and the upper jaw part, provided that this movable connection allows that, by moving the lower and the upper jaw parts relative to each other, a gripping movement is performed. This means that it shall be possible to increase or decrease the distance of the upper jaw part from the lower jaw part at least along a connecting line. The joint can be formed as a pivot joint (hinge), screw joint, rotational sliding joint, ball joint, universal joint, sliding joint or also in a different way in which joints can be designed. In the case of a pivot joint, the lower jaw part and the upper jaw part are rotatable about said joint. In the case of a screw joint, the distance of the upper jaw part from the lower jaw part can be changed, wherein at least the upper jaw part and the lower jaw part remain aligned substantially parallel to each other.

Both the first pair of coagulation sections and also the second pair of coagulation sections, respectively, comprise a lower coagulation section as well as an upper coagulation section, wherein a lower coagulation section is generally provided on the lower jaw part, while an upper coagulation section is provided on the upper jaw part.

Here, two different embodiments are conceivable. On the one hand, the first lower coagulation section, the first upper coagulation section, the second lower coagulation section and the second upper coagulation section can be implemented in each case as a separate electrode, wherein each electrode has its own electrical connection. The connections of the electrodes can either be fed within the instrument to an electrically conductive connection or they can be separately fed out of the instrument and led to a power supply unit. On the other hand, however, it is also possible to implement the respective coagulation sections arranged in a jaw part as parts of a single continuous electrode. This mode can be implemented for the lower coagulation sections as well as for the upper coagulation sections and likewise for the lower as well as for the upper coagulation sections. For example, the coagulation sections can then be formed as lever arms of a U-shaped electrode.

Preferably, the first lower coagulation section is aligned parallel to the second coagulation section. Likewise, the first upper coagulation section is preferably aligned parallel to the second upper coagulation section.

In case tissue is between an upper coagulation section and a lower coagulation section and coming into contact with the two respective sections, heating and thus coagulation of the interstitial tissue can be achieved by applying a typically high-frequency voltage. If this involves here, for example, a blood-conveying vein, the vein can be closed at the respective place in order to prevent the blood from flowing out. If a blood-conveying vein is coagulated both by the first pair of coagulation sections as well as the second pair of coagulation sections, blooding is prevented at both places. The interstitial tissue remains intact for the time being.

By means of the at least one bipolar pair of cutting electrodes between the first pair of coagulation sections and the second pair of coagulation sections, the interstitial tissue can be cut. For this, a voltage is applied between at least two electrodes of the at least one bipolar pair of cutting electrodes so that current flows through the tissue. For this purpose, at least two electrodes have to come in contact with the tissue. The current flowing through the tissue rapidly heats the cell fluid and provides for an increasing vapor pressure within the cells. Thereby, the cell walls are ruptured. Preferably, this cutting process is performed after coagulation. However, other sequences are also conceivable.

Particularly effective is the cutting process if the current flow forms an arc. In order to generate such an arc, preferably one electrode can have a significantly smaller surface toward the tissue than an oppositely poled electrode. Due to the high voltage which is generated at the electrode having a smaller surface, the ignition of an arc is facilitated.

Preferably, the electrosurgical gripping instrument is configured for cutting tissue along a cutting line. Such a cutting line can be a straight path, but it can also be curved, zigzag-shaped or shaped in any other manner. The bipolar pair of cutting electrodes or, optionally, a plurality of pairs of cutting electrodes, has then to be formed adequately in order to effect the cutting process along the cutting line.

According to one embodiment, the electrosurgical gripping instrument has exactly one pair of cutting electrodes with exactly two electrodes, namely with a first cutting electrode and a second cutting electrode. Preferably, the first cutting electrode and the second cutting electrode are arranged on both sides of an insulator and respectively have a cutting edge extending along the cutting line. This ensures that current flows between the first cutting electrode and the second cutting electrode through the tissue to be cut and that the tissue is cut along the cutting line. Further preferred, the two cutting edges extend parallel to each other. Provided that the tissue is approximately uniform, a uniform cutting effect along the cutting line is achieved.

According to another preferred embodiment, the first cutting electrode is arranged at the lower jaw part and the second cutting electrode is arranged at the upper jaw part, wherein the first cutting electrode and the second cutting electrode have one cutting edge, respectively, and wherein the cutting edges extend along the cutting line and face each other. In this embodiment, the tissue to be cut has to be brought between the first cutting electrode and the second cutting electrode, and, with suitable contact and current flow, is cut along the cutting line. In contrast to the embodiment in which the first cutting electrode and the second cutting electrode are arranged on both sides of an insulator, in the embodiment with the cutting edges facing each other it is not required that the tissue on one side contacts two electrodes. Rather, the contact is generated through pressure from two sides. As a result, the cutting effect can be improved.

In an embodiment with opposing cutting electrodes, preferably an electrically insulating spacer is provided which prevents a contact between the electrodes.

According to a further preferred embodiment, the bipolar pair of cutting electrodes is a pair of cutting electrodes arranged at the lower jaw part, with a first lower cutting electrode and a second lower cutting electrode, which are arranged on both sides of a lower insulator. Further, on the upper jaw part, an upper pair of cutting electrodes is arranged, having a first upper cutting electrode and a second upper cutting electrode which are arranged on both sides of an upper insulator. The first lower cutting electrode, the second lower cutting electrode, the first upper cutting electrode and the second upper cutting electrode have a cutting edge, respectively. The cutting edges extend along the cutting line.

In this embodiment, the electrosurgical gripping instrument has a total of two pairs of cutting electrodes which face each other. Typically, two of the total of four electrodes are used as electrodes of first polarity, whereas, in comparison, the two other electrodes are used as electrodes of second polarity with a polarity opposite the first polarity. The two electrodes of first polarity can be arranged on the same side of the tissue, on different sides of the tissue and directly opposing, or on different sides of the tissue and diagonally opposing. Depending on the configuration, a current flow through the tissue in two directions can be achieved.

It is to be understood that polarity not necessarily means a fixed potential or a fixed sign. Rather, voltages and regularly also the signs of the voltages of the electrodes of first polarity and of the electrodes of second polarity will constantly change at alternating voltage, but be opposite to each other.

In this embodiment, too, the cutting edges preferably extend parallel to each other. In the case of approximately uniform tissue, this results in a uniform cutting effect.

In all embodiments in which one or two pairs of cutting electrodes are used, the respective cutting electrodes are preferably flat, i.e. plate-shaped. This allows a simple fabrication. This applies in particular for cutting electrodes being arranged laterally of an insulator.

According to an alternative embodiment, the bipolar pair of cutting electrodes is one of a multiplicity of pairs of cutting electrodes with a first cutting electrode and a second cutting electrode, respectively, wherein first cutting electrodes and second cutting electrodes are alternatively arranged alternately along the cutting line on a jaw part. Thereby, a respective current flow is locally achieved between two adjacent cutting electrodes, whereby the tissue is cut along the cutting lines. Thereby, the first cutting electrodes can all be connected at the same time to a first pole of an electrical source, while the second cutting electrodes are all connected at the same time to a second pole of the electrical source. However, as an alternative, also the first and second cutting electrodes can be connected to the electrical source by means of a switching device, for example a multiplexer. The switching device allows to successively connect the connected pairs of cutting electrodes to the electrical source. Thereby, a controlled cutting movement from one end of the cutting line to the other end of the cutting line can be performed.

The cutting line can be aligned parallel to the first pair of coagulation sections and/or to the second pair of coagulation sections. Thus, a simple geometry within the gripping instrument can be achieved.

According to a modification, the electrosurgical gripping instrument further comprises a plurality of opposing pairs of cutting electrodes on a jaw part that opposes a jaw part on which already a multiplicity of pairs of cutting electrodes is provided. The opposing pairs of cutting electrodes each have an opposing first cutting electrode and an opposing second cutting electrode. The opposing first cutting electrodes and the opposing second cutting electrodes are alternately arranged along an opposing cutting line.

It is to be understood that the term "opposing" is here principally used with regard to a tissue inserted as intended as a reference surface.

Preferably, surfaces of the coagulation sections, which face toward the respective other coagulation section of the respective coagulation pair, are larger than surfaces of the cutting electrodes of the pair of cutting electrodes which face toward a jaw part to which the respective cutting electrode is not attached. This considers the fact that coagulation shall regularly take place over a larger region than the cutting process. Moreover, for the cutting process, a beneficial arc that can be achieved easier with a smaller surface.

Further advantages and embodiments of the invention become obvious for the person skilled in the art by the following exemplary embodiments which are described with reference to the attached drawings.

Figure 1:
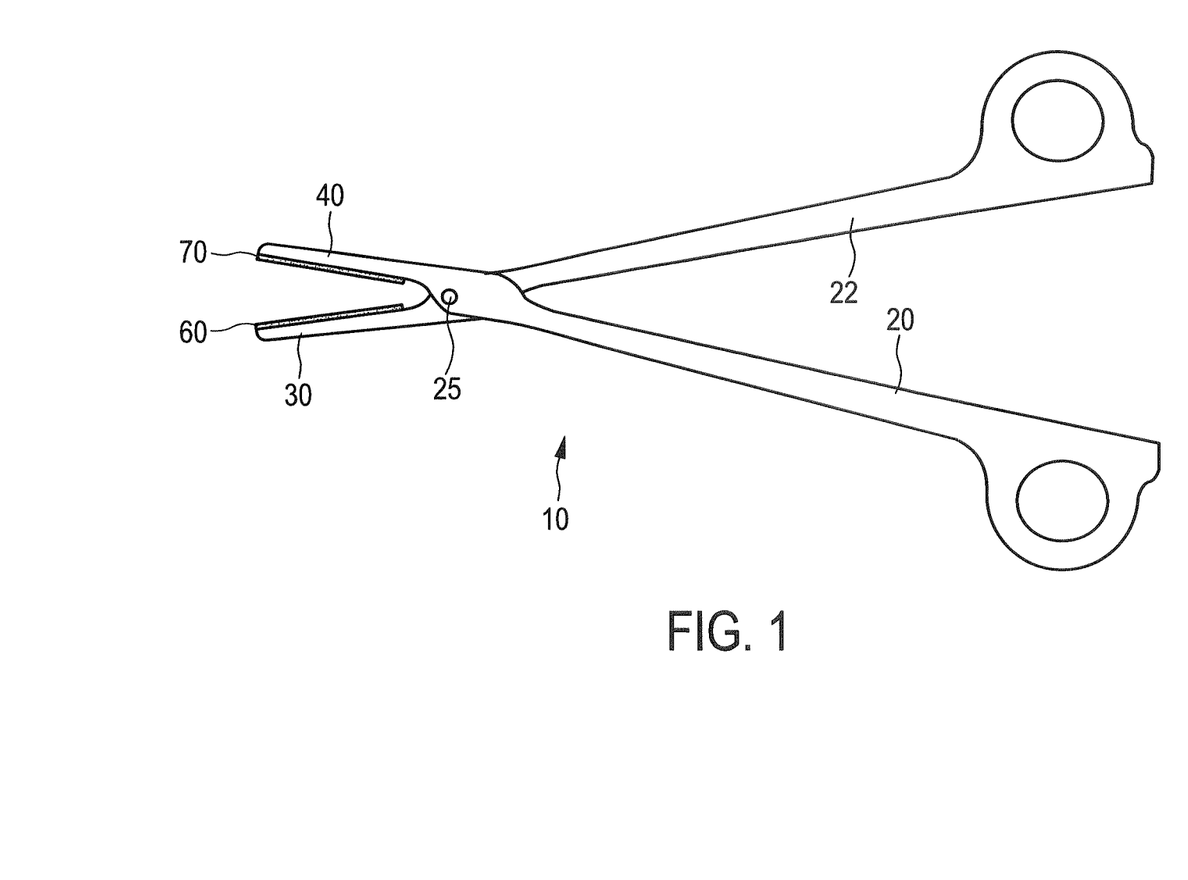
FIG. 1 shows a state of the art electrosurgical gripping instrument.

FIG. 1 shows an electrosurgical gripping instrument 10 according to the prior art. It comprises a first handle part 20, a second handle part 22, a lower jaw part 30 connected to the second handle part 22 and an upper jaw part 40 connected to the first handle part 20.

The upper jaw part 40 is rotatable relative to the lower jaw part 30 by means of a hinge 25 so that the upper jaw part 40 together with the lower jaw part 30 can perform a forcipate gripping movement when the second handle part 22 is pressed against the first handle part 20.

On the lower jaw part 30, a lower electrode arrangement 60 is attached which faces toward the upper jaw part 40. On the upper jaw part 40, an upper electrode arrangement 70 is attached which faces toward the lower jaw part 30. Together, the lower electrode arrangement 60 and the upper electrode arrangement 70 form the electrode arrangement of the electrosurgical gripping element.

Figure 2:
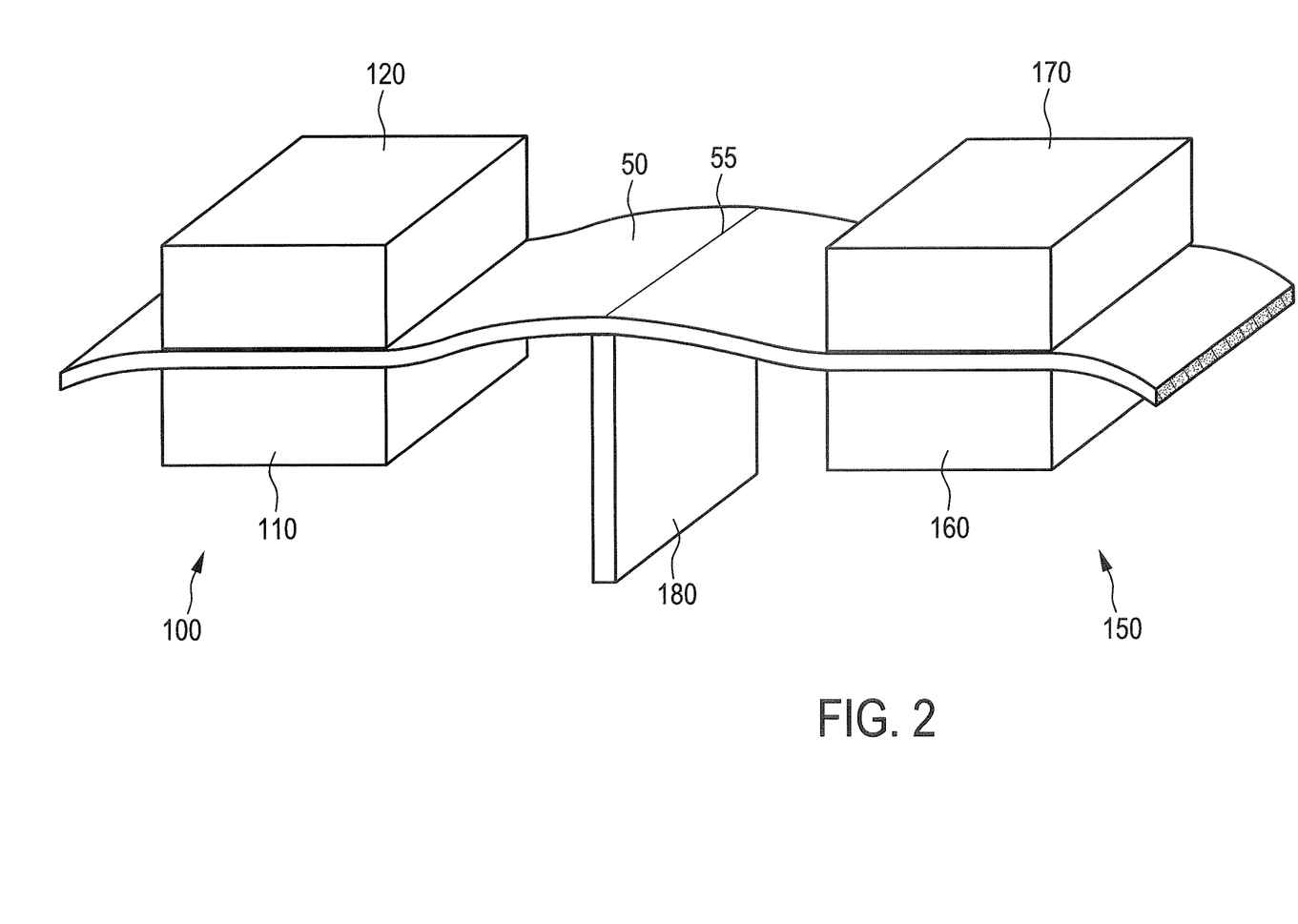
FIG. 2 shows a state of the art electrode arrangement of an electrosurgical gripping instrument.

FIG. 2 shows schematically an electrode arrangement of the electrosurgical gripping element of FIG. 1. The electrodes are in a position which corresponds to the one when the upper jaw part 40 is folded in or closed with regard to the lower jaw part 30.

A first pair 100 of coagulation sections and a second pair 150 of coagulation sections are attached on the jaw parts 30, 40. The first pair 100 of coagulation sections has a first lower coagulation section 110 and a first upper coagulation section 120. The first lower coagulation section 110 is located on the lower jaw part 30, whereas the first upper coagulation section 120 is located on the upper jaw part 40. Furthermore, a cutting electrode 180 is located in the lower jaw part 30.

The second pair 150 of coagulation sections has a second lower coagulation section 160 and a second upper coagulation section 170. The second lower coagulation section 160 is located on the lower jaw part 30, whereas the second upper coagulation section 170 is located on the upper jaw part 40.

The first lower coagulation section 110 and the first upper coagulation 120 are arranged such that they are aligned to directly adjoin each other when the upper jaw part 40 is folded relative to the lower jaw part 30. The same applies to the second lower coagulation section 160 and the second upper coagulation section 170. The first pair 100 of coagulation sections and the second pair 150 of coagulation sections thus can conduct current through interstitial tissue in order to achieve a coagulation effect.

Between the coagulation sections 100, 150 and abutting on the cutting electrode 180 is a piece of tissue 50 which is to be coagulated and cut. During regular usage, the tissue 50 is firstly coagulated between the pairs 100, 150 of coagulation sections. Subsequently, between the cutting electrode 180 and one of the coagulation sections 110, 120, 160, 170, a voltage is applied which generates a current flow. While current flows through the tissue 50, the tissue 50 is heated at least along a cutting line 55 and thus cut, because there the current density is highest. Also, forming an arc, that is advantageous for cutting, is possible.

However, the current thereby has to flow through already coagulated and thus dry tissue which usually has a higher resistance than the non-coagulated tissue. Thus, a significant portion of the applied voltage drops across the coagulated tissue and is no longer available for heating of the tissue to be cut.

Figure 3:
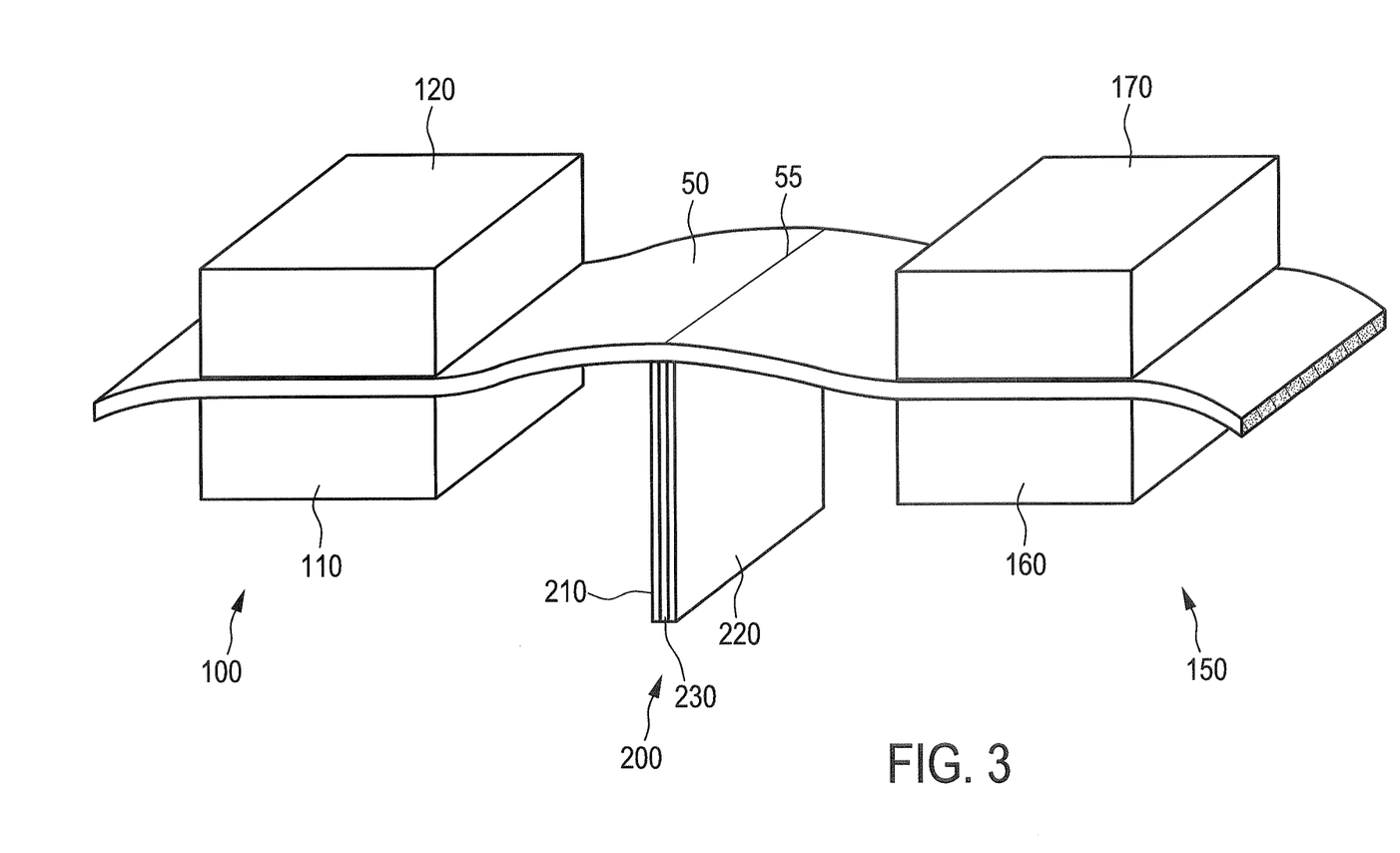
FIG. 3 shows an electrode arrangement according to a first embodiment of the invention.

FIG. 3 shows an electrode arrangement of an electrosurgical gripping instrument according to a first embodiment of the invention. The first pair 100 of coagulation sections and the second pair 150 of coagulation sections do not differ from the embodiment shown in FIG. 2. However, in the embodiment according to FIG. 3, instead of the cutting electrode 180, a bipolar pair 200 of cutting electrodes having a first cutting electrode 210 and a second cutting electrode 220 is used. The first cutting electrode 210 and the second cutting electrode 220 have a flat shape. They are arranged on both sides of an also flat-shaped insulator 230 that electrically separates the first cutting electrode 210 and the second cutting electrode 220.

As illustrated, the tissue 50 to be cut extends directly above the pair of cutting electrodes 200 and is also contacted by the first cutting electrode 210 and the second cutting electrode 220. In fact, the contact between the tissue 50 and the cutting electrodes 210, 220 thus takes place along a respective cutting edge which is formed by the respective upper end of the respective cutting electrode. Because of being covered by the tissue 50, the cutting edges are not visible in FIG. 3.

During regular operation for closing veins, again the tissue is at first coagulated between the first pair 120 of coagulation sections and the second pair 150 of coagulation sections. Subsequently, a current is conducted through the tissue 50 between the first cutting electrode 210 and the second cutting electrode 220. The current does not have to flow through an already coagulated tissue section, but rather can flow exactly along the desired cutting line 55 through a not yet treated and thus moist tissue portion 50. Thereby, a more uniform local heating of the tissue 50 along the cutting line 55 can be achieved. Areas of significantly increased resistance are no longer within the current flow.

Figure 4:
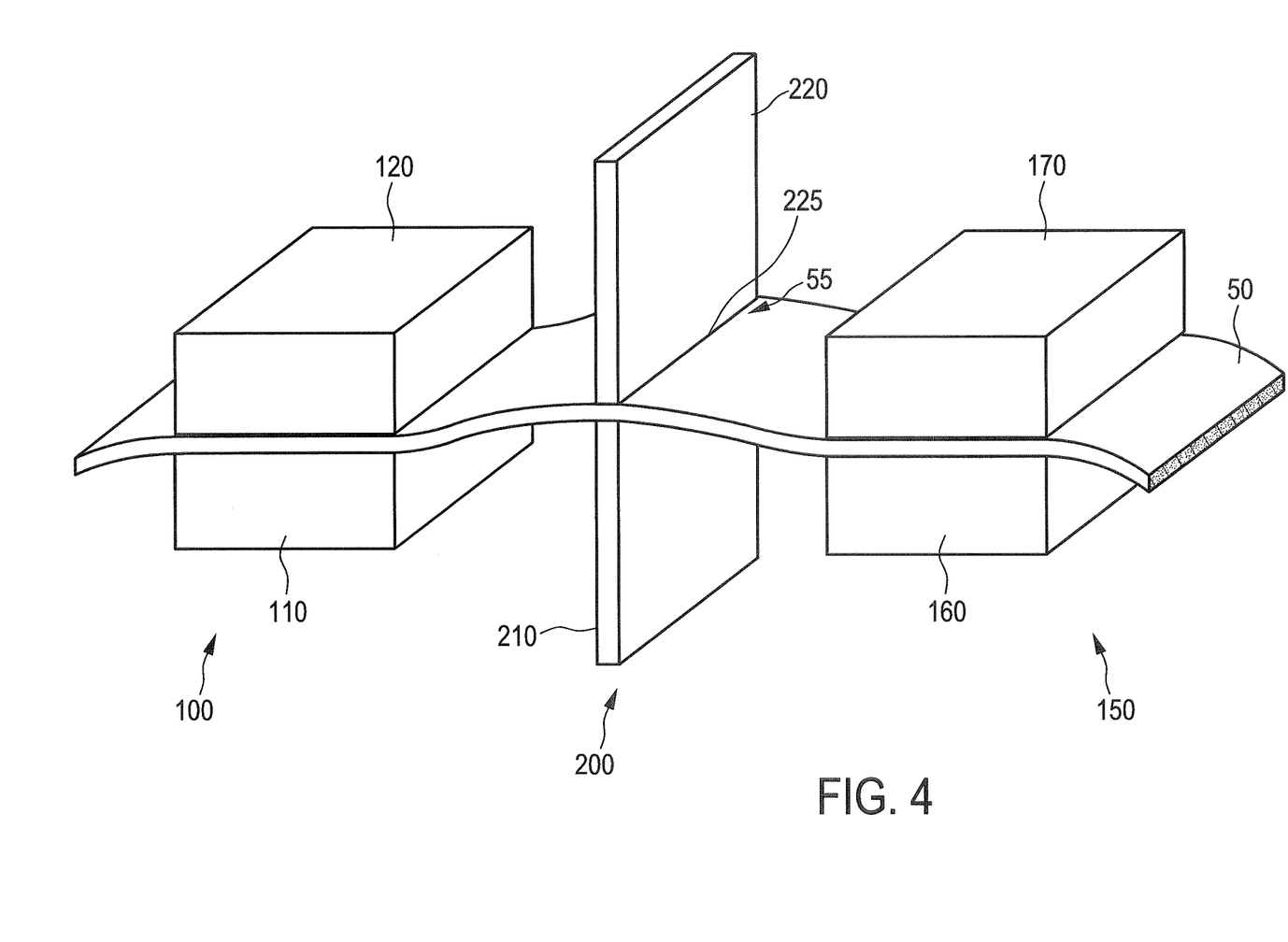
FIG. 4 shows an electrode arrangement according to a second embodiment of the invention.

FIG. 4 shows an alternative embodiment which, compared to the embodiment in FIG. 3, is modified in that the first cutting electrode 210 and the second cutting electrode 220 of the pair of cutting electrodes 200 are no longer arranged on both sides of an insulator, but oppose each other. Here, the first cutting electrode 210 is attached on the lower jaw part 30, whereas the second cutting electrode 220 is attached on the upper jaw part 40. This illustration shows a cutting edge 225 of the second cutting electrode 220, which cutting edge, extending along the cutting line 55, comes into contact with the tissue 50. In the embodiment according to FIG. 4, the current for cutting likewise flows between the first cutting electrode 210 and the second cutting electrode 220; however, in comparison to the direction in which the current flows in an embodiment according to FIG. 3, it flows now in a direction transverse thereto. Thus, in this direction, the tissue 50 is in any case completely cut through along the cutting edge 55. Moreover, a contact can be reliably established by sufficiently pressing the first cutting electrode 210 against the second cutting electrode 220. In a non-illustrated alternative embodiment, one surface of the cutting electrodes is different so that an arc ignites at one of the electrodes.

Figure 5:
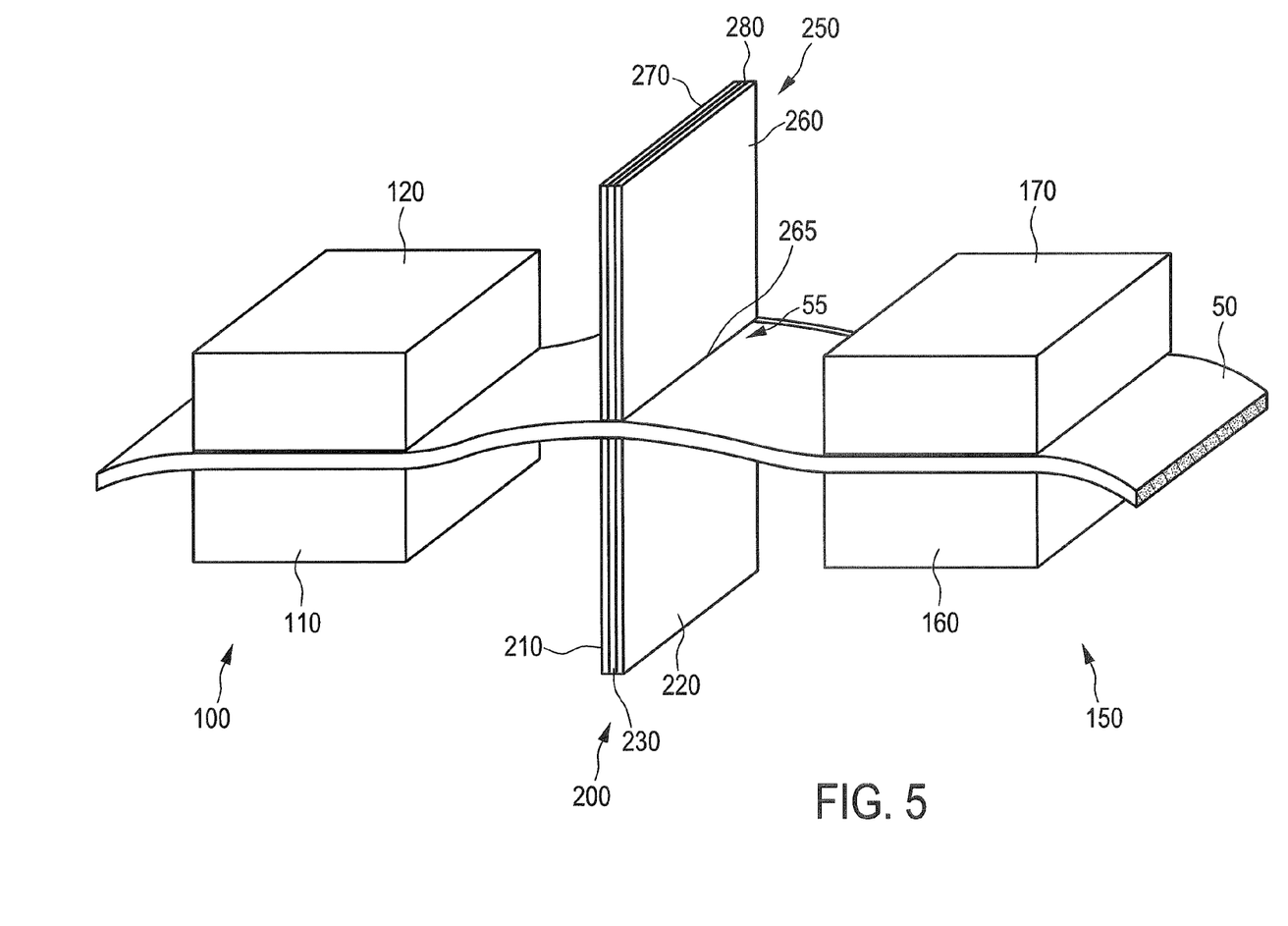
FIG. 5 shows an electrode arrangement according to a third embodiment of the invention.

FIG. 5 shows a further embodiment of the invention. As in the embodiment according to FIG. 3, a pair 200 of cutting electrodes is attached on the lower jaw part 30. In the embodiment according to FIG. 5, this pair 200 of cutting electrodes is designated as lower pair 200 of cutting electrodes having a first lower cutting electrode 210 and a second lower cutting electrode 220. Likewise, the insulator 230 is designated as lower insulator 230.

In the embodiment according to FIG. 5, an upper pair 250 of cutting electrodes is provided on the upper jaw part 40 in addition to the lower pair 200 of cutting electrodes, which upper pair of cutting electrodes has a first upper cutting electrode 260 and a second upper cutting electrode 270. The first upper cutting electrode 260 and the second upper cutting electrode 270 as well as the first lower cutting electrode 210 and the second lower cutting electrode 220 are arranged on both sides of an insulator, namely an upper insulator 280.

Through the arrangement according to FIG. 5, current can not only flow in one direction through the tissue 50, but in two directions extending transversely to each other. Thereby, a particularly good and uniform cutting effect is achieved.

If opposing electrodes have the same polarity, a short circuit is avoided even if the electrodes come into contact with each other.

Figure 6:
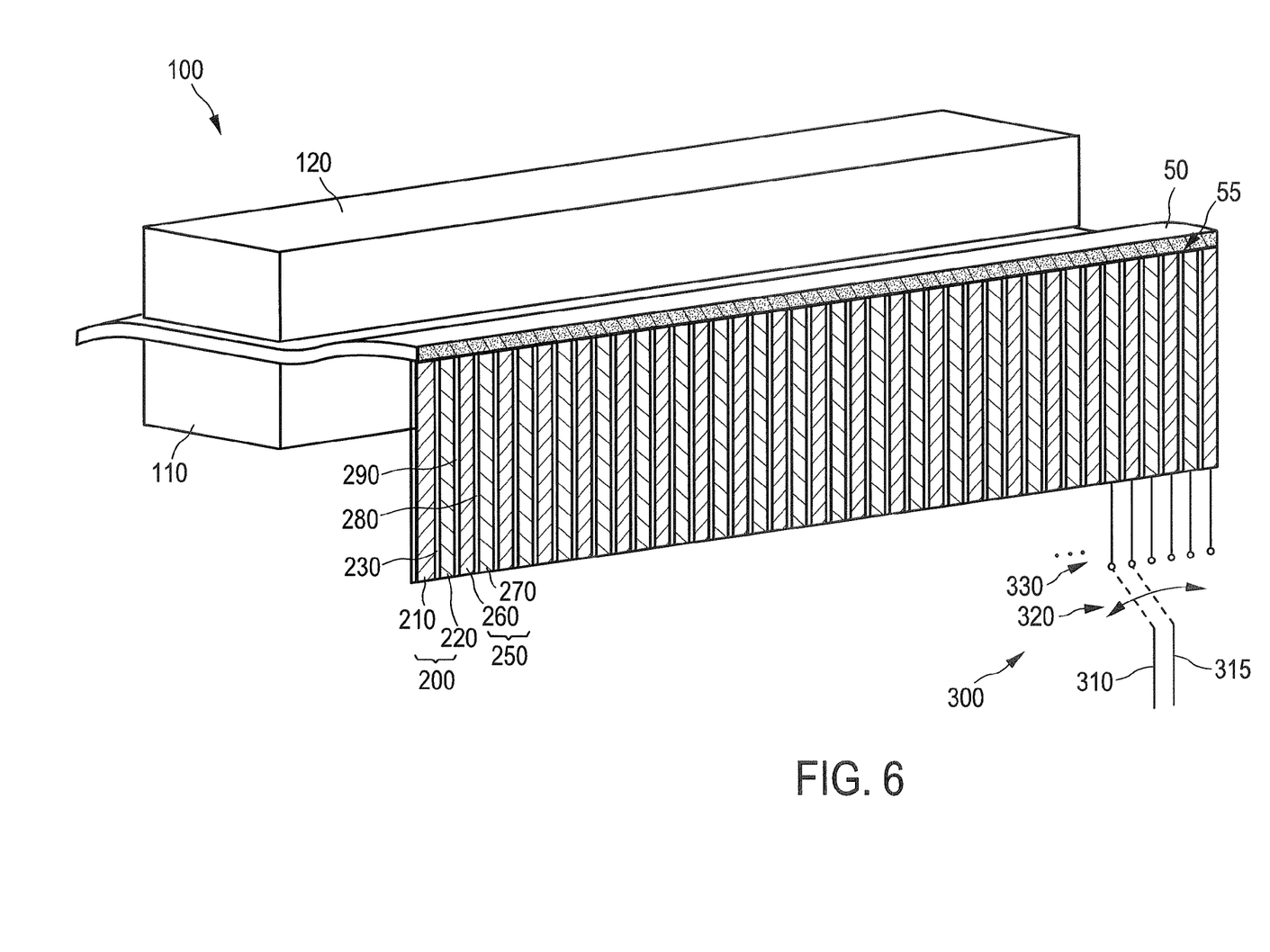
FIG. 6 shows an electrode arrangement according to a fourth embodiment of the invention.

FIG. 6 shows a further embodiment of the invention. In contrast to the previously shown embodiments, in the embodiment according to FIG. 6, a plurality of pairs of cutting electrodes is provided. As an example, a first pair 200 of cutting electrodes with a first cutting electrode 210 and a second cutting electrode 220 as well as a second pair 250 of cutting electrodes with a further first cutting electrode 260 and a further second cutting electrode 270 are to be mentioned here. The electrodes of the first pair 200 of cutting electrodes are separated by a first insulator 230, whereas the electrodes of the second pair 250 of cutting electrodes are separated by a further insulator 280. Also, between the first pair 200 of cutting electrodes and the second pair 250 of cutting electrodes, an electrical insulation is necessary which is implemented through an insulator 290.

The arrangement of first and second cutting electrodes continues alternating along the cutting line 55, as shown in FIG. 6. Thus, the current flow substantially always takes place between two adjacent cutting electrodes, wherein the tissue 50 is cut along the cutting line 55.

The power supply to the cutting electrodes can be implemented such that the first cutting electrodes are connected to a common pole of an electrical HF source, thus, e.g., an HF generator, and the second cutting electrodes are connected to another common pole of the electrical source. However, this case is not illustrated in FIG. 6.

Rather, FIG. 6 shows a multiplexer 300 which can be used in order to selectively connect one of a plurality of first and second cutting electrodes to the HF generator, respectively. The multiplexer 300 has a first line 310 and a second line 315 to the HF generator (not illustrated) which can be connected by means of a switching unit 320 to one of a plurality of contacts of a contact row 330. The multiplexer 300 is only schematically illustrated in FIG. 6. It is to be understood that the other first and second cutting electrodes can also be supplied by means of the same or another multiplexer.

Figure 7:
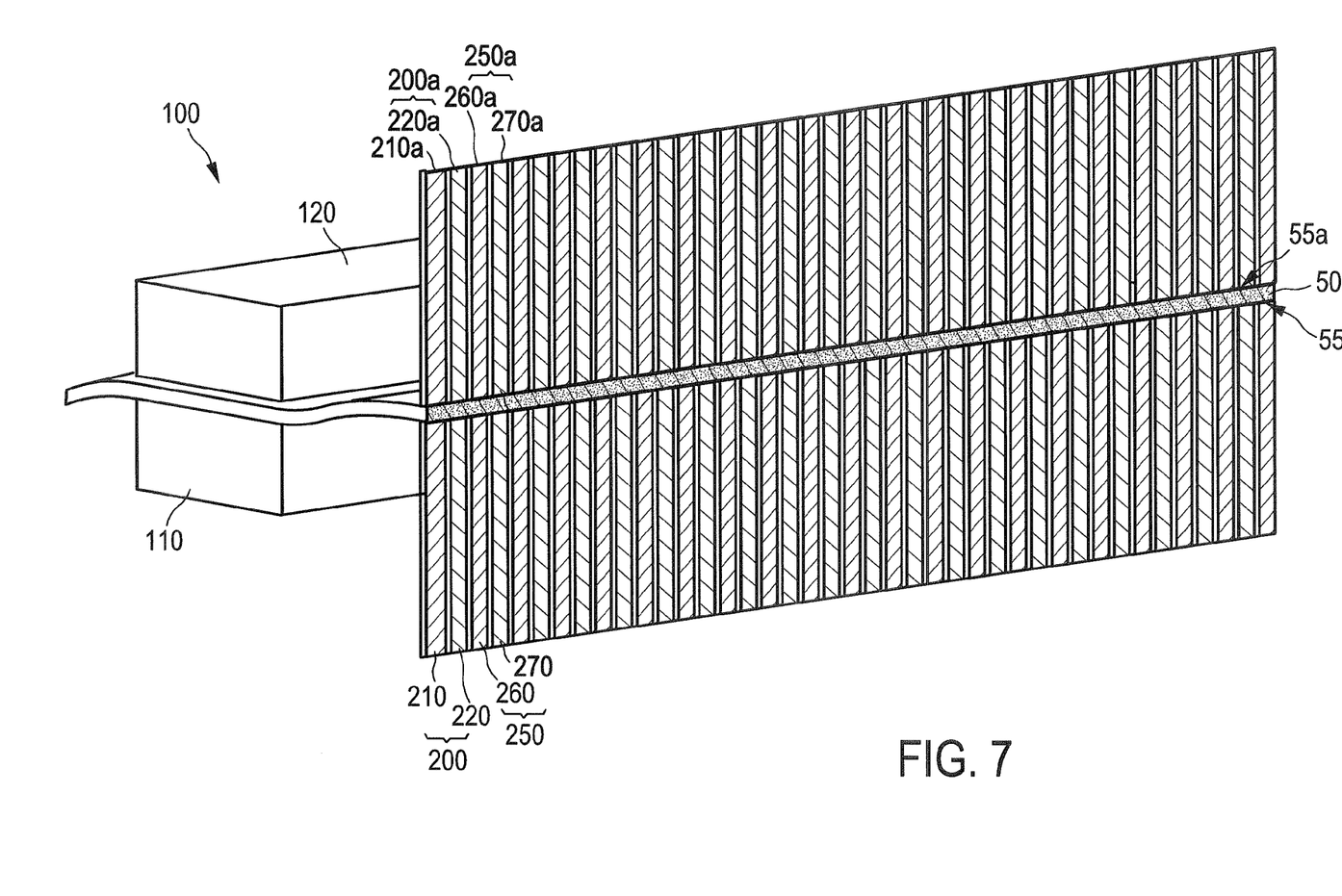
FIG. 7 shows an electrode arrangement according to a fifth embodiment of the invention.

FIG. 7 shows a further embodiment which differs from the embodiment illustrated in FIG. 6 in such that, in addition to the plurality of pairs of cutting electrodes, which in the embodiment of FIG. 6 are only on one side of the tissue, a further row with a plurality of pairs of cutting electrodes is arranged on the opposite side with regard to the tissue. Said further row of pairs of cutting electrodes can cut the tissue along an opposing cutting line 55a. Again as an example, an opposing first pair 200a of cutting electrodes with an opposing first cutting electrode 210a and an opposing second cutting electrode 220a as well as an opposing second pair 250a of cutting electrodes with an opposing further first cutting electrode 260a and an opposing further second cutting electrode 270a are to be mentioned here. Apart from that, the structure of the opposing electrodes is identical to the electrodes already illustrated in the embodiment of FIG. 6. Here, it is particularly advantageous if the respective opposing cutting electrodes 210, 220, 260, 270 and 210a, 220a, 260a, 270a have a different polarity. Hereby, a particularly good cutting effect is achieved.

Figure 8:
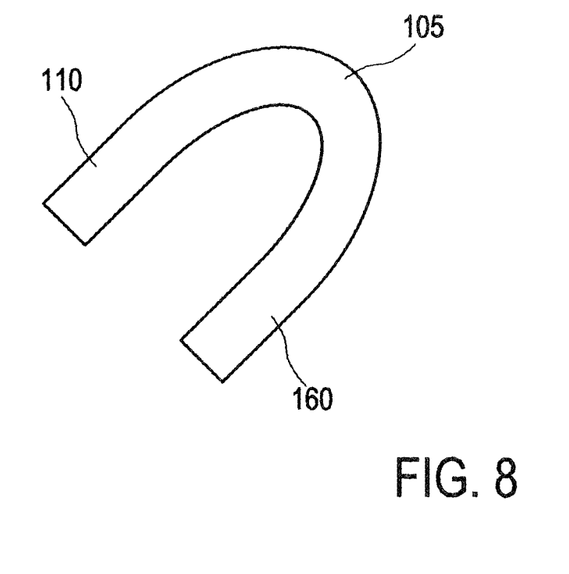
FIG. 8 shows an alternative embodiment of two lower coagulation sections.

FIG. 8 shows an alternative embodiment of the first lower coagulation section 110 and the second lower coagulation section 160 with a single, continuously conductive electrode. In principle, this embodiment is alternatively applicable in all previously shown exemplary embodiments. Here, the first lower coagulation section 110 and the second lower coagulation section 160 are formed as an integral part of a continuous, here exemplarily U-shaped electrode 105. Thus, a separate electrical contacting of the first lower coagulation section 110 and the second lower coagulation section 160 is obsolete.

The embodiment for the lower coagulation sections shown in FIG. 8 can also be applied to the upper coagulation sections. The arrangement of cutting electrodes in such an embodiment relative to the coagulation sections does not differ from the previous embodiments.

REFERENCE LIST

10 Electrosurgical gripping instrument
20 First handle part
22 Second handle part
25 Hinge
30 Lower jaw part
40 Upper jaw part
50 Tissue
55 Cutting line
55a Opposing cutting line
60 Lower electrode arrangement
70 Upper electrode arrangement
100 First pair of coagulation sections
105 Electrode
110 First lower coagulation section
120 First upper coagulation section
150 Second pair of coagulation sections
160 Second lower coagulation section
170 Second upper coagulation section
180 Cutting electrode
200 Pair of cutting electrodes
200a Opposing pair of cutting electrodes
210 First/first lower cutting electrode
210a Opposing first cutting electrode
220 Second/second lower cutting electrode
220a Opposing second cutting electrode
225 Cutting edge
230 Insulator
250 Upper/further pair of cutting electrodes
250a Opposing further pair of cutting electrodes
260 First upper/further first cutting electrode
260a Opposing further first cutting electrode
265 Cutting edge
270 Second upper/further second cutting electrode
270a Opposing further second cutting electrode
280 Upper/further insulator
290 Insulator
300 Multiplexer
310 First line to a HF generator
315 Second line to a HF generator
320 Switching unit
330 Contact row

The invention claimed is:

1. Electrosurgical gripping instrument, comprising:
a handle part;
a lower jaw part and an upper jaw part, which can perform a forcipate movement; a first pair of coagulation sections comprising a first lower coagulation section on the lower jaw part and a first upper coagulation section on the upper jaw part;
a second pair of coagulation sections comprising a second lower coagulation section on the lower jaw part and a second upper coagulation section on the upper jaw part; and
at least one bipolar pair of cutting electrodes between the first pair of coagulation sections and the second pair of coagulation sections, wherein
surfaces of the first lower coagulation section and the first upper coagulation section, which face each other, and surfaces of the second lower coagulation section and the second upper coagulation section, which face each other, are larger than surfaces of each of the cutting electrodes of the bipolar pair of cutting electrodes, which faces one of the lower jaw part and the upper jaw part on which the respective cutting electrode is not attached,
the instrument is configured to cut tissue along a cutting line, and
the at least one bipolar pair of cutting electrodes includes a first cutting electrode and a second cutting electrode that are laterally arranged on opposite sides of an insulator, and the first cutting electrode and the second cutting electrode each have one cutting edge extending along the cutting line.

2. The electrosurgical gripping instrument according to claim 1, wherein
the instrument has exactly one bipolar pair of cutting electrodes with exactly two electrodes, the two electrodes comprising the first cutting electrode and the second cutting electrode.

3. The electrosurgical gripping instrument according to claim 2, wherein
the first cutting electrode is attached on the lower jaw part and the second cutting electrode is attached on the upper jaw part,
the first cutting electrode and the second cutting electrode, respectively, have one cutting edge, and
the cutting edges extend along the cutting line and face each other.

4. The electrosurgical gripping instrument according to claim 2,
wherein the first cutting electrode and the second cutting electrode are formed flat.

5. The electrosurgical gripping instrument according to claim 1,
wherein the two cutting edges extend parallel to each other.

6. The electrosurgical gripping instrument according to claim 1, wherein
the instrument is designed for cutting tissue along a cutting line,
the bipolar pair of cutting electrodes includes a pair of cutting electrodes attached on the lower jaw part, said pair of cutting electrodes comprising a first lower cutting electrode and a second lower cutting electrode which are arranged on opposite sides of a lower insulator,
the instrument further includes an upper pair of cutting electrodes attached on the upper jaw part, the upper pair of cutting electrodes comprising a first upper cutting electrode and a second upper cutting electrode which are arranged on opposite sides of an upper insulator,
the first lower cutting electrode, the second lower cutting electrode, the first upper cutting electrode, and the second upper cutting electrode, respectively, have one cutting edge, and
the cutting edges extend along the cutting line.

7. The electrosurgical gripping instrument according to claim 6,
wherein the cutting edges extend parallel to each other.

8. The electrosurgical gripping instrument according to claim 1, wherein
the instrument is designed for cutting tissue along a cutting line,
the bipolar pair of cutting electrodes is one of a plurality of pairs of cutting electrodes on a first one of the upper jaw part and the lower jaw part, each of the pairs of the cutting electrodes comprising a first cutting electrode and a second cutting electrode, respectively, and
the first cutting electrodes and the second cutting electrodes are arranged alternately along the cutting line.

9. The electrosurgical gripping instrument according to claim 8, wherein
the instrument is designed for cutting tissue along an opposing cutting line,
the instrument further comprises a plurality of opposing pairs of cutting electrodes on a second one of the upper jaw part and the lower jaw part, each of the opposing pairs of the cutting electrodes comprising an opposing first cutting electrode and an opposing second cutting electrode, respectively, and
the opposing first cutting electrodes and the opposing second cutting electrodes are arranged alternately along the opposing cutting line.

10. The electrosurgical gripping instrument according to claim 8,
wherein the first cutting electrodes are connected to a first pole of an electrical high frequency source and the second cutting electrodes are connected to the second pole of the electrical high frequency source.

11. The electrosurgical gripping instrument according to claim 10,
wherein one of the first cutting electrodes and one of the second cutting electrodes are connected simultaneously via a switch to the electrical high frequency source.

12. The electrosurgical gripping instrument according to claim 8,
wherein the first cutting electrodes are connected to a first electrical high frequency source and the second cutting electrodes are connected to a second electrical high frequency source.

13. Electrosurgical gripping instrument, comprising:
a handle part;
a lower jaw part and an upper jaw part, which can perform a forcipate movement; a first pair of coagulation sections comprising a first lower coagulation section on the lower jaw part and a first upper coagulation section on the upper jaw part;
a second pair of coagulation sections comprising a second lower coagulation section on the lower jaw part and a second upper coagulation section on the upper jaw part; and
at least one bipolar pair of cutting electrodes between the first pair of coagulation sections and the second pair of coagulation sections, wherein
the instrument is designed for cutting tissue along a cutting line, the at least one bipolar pair of cutting electrodes has a first cutting electrode and a second cutting electrode that are laterally arranged on opposite sides of an insulator and respectively have one cutting edge extending along the cutting line, and the first cutting electrode and the second cutting electrode of the at least one bipolar pair of cutting electrodes are arranged on a same side of the tissue to be cut.

\* \* \* \* \*